United States Patent [19]

Maruo et al.

[11] Patent Number: 5,624,667
[45] Date of Patent: Apr. 29, 1997

[54] TITANIUM OXIDE PARTICLES AND METHOD OF PRODUCING SAME

[75] Inventors: Masatsuyo Maruo; Hitoshi Ando; Mitsuru Watanabe; Chitoshi Mukai, all of Kusatsu, Japan

[73] Assignee: Ishihara Sangyo Kaisha, Ltd., Osaka, Japan

[21] Appl. No.: 405,134

[22] Filed: Mar. 16, 1995

Related U.S. Application Data

[63] Continuation-in-part of Ser. No. 69,416, Jun. 1, 1993, Pat. No. 5,480,636.

[30] Foreign Application Priority Data

| Jun. 3, 1992 | [JP] | Japan | 4-168380 |
| Nov. 12, 1992 | [JP] | Japan | 4-327342 |

[51] Int. Cl.$^6$ ............................................. A61L 9/20
[52] U.S. Cl. .................. 424/76.21; 424/76.1; 424/617; 424/641
[58] Field of Search ................. 424/76.2, 76.1, 424/617, 641, 724

[56] References Cited

U.S. PATENT DOCUMENTS 3,640,743  2/1972  Sheehan ............................. 106/300

FOREIGN PATENT DOCUMENTS

| 1350550 | 12/1963 | France . |
| 2140711 | 2/1972 | Germany . |
| 61-135669 | 6/1986 | Japan . |
| 63-186445 | 8/1988 | Japan . |
| 63-302856 | 12/1988 | Japan . |
| 2-95436 | 4/1990 | Japan . |
| 3-33022 | 5/1991 | Japan . |
| 4-26893 | 5/1992 | Japan . |
| 545604 | 6/1942 | United Kingdom . |
| 581008 | 9/1946 | United Kingdom . |

OTHER PUBLICATIONS

Chemical Abstracts, vol. 84, No. 12, Mar. 22, 1976, Abstract No. 75835u, p. 96, col L, & SU-A-492529 (Nov. 25, 1975).
Chemical Abstracts, vol. 105, No. 16, Oct. 1986, Abstract No. 135557u, p. 87, col L, & Takeshima et al, 1986.
Database WPI, Derwent Publications Ltd. Class A60 AN 91-300334 & JP-A-3 200 878, Sep. 2, 1991.

*Primary Examiner*—Jyothsna Venkat
*Attorney, Agent, or Firm*—Cushman Darby & Cushman IP Group of Pillsbury Madison & Sutro LLP

[57] ABSTRACT

Titanium oxide particles comprising particulate titanium oxide substrate having a zinc oxy compound or a combination of a zinc oxy compound and a silicon oxy compound supported thereon. They can be produced by adding a zinc compound or a combination of a zinc compound and a silicon compound together with an alkali to a dispersion of particulate titanium oxide substrate to neutralize the zinc compound or the combination of the zinc compound and the silicon compound in said dispersion, then separating and drying the resultant product. They are useful for pigments, catalysts, catalyst supports and adsorbents, and particularly excellent in deodorizing performance by removing malodorous gases such as ammonia, methyl mercaptan, hydrogen sulfide, trimethylamine, methyl sulfide and acetaldehyde through decomposition and adsorption thereof, so that they are useful as white deodorants for sanitary objects such as paper diaper and sanitary napkins which come to directly contact with the skins of human beings.

2 Claims, 2 Drawing Sheets

TITANIUM OXIDE PARTICLES AND METHOD OF PRODUCING SAME

This is a continuation-in-part application of U.S. application Ser. No. 08/069,416 filed on Jun. 1, 1993 now U.S. Pat. No. 5,480,636, all disclosure of which is incorporated herein by reference.

BACKGROUND OF THE INVENTION

1. Field of the Invention

The present invention relates to titanium oxide particles useful for pigments, catalysts, catalyst supports, adsorbents and the like, and more particularly, to titanium oxide particles having a high specific surface area useful for deodorants adsorbing obnoxious gases such as ammonia, mercaptans, hydrogen sulfide and aldehydes as well as for scavengers capable of removing noxious materials by decomposing them through photocatalytic reaction.

2. Description of Related Art

Obnoxious gases widely produced in inhabitant environments include ammonia, methyl mercaptan, hydrogen sulfide, trimethylamine, methyl sulfide, and acetaldehyde. An attempt has been made to remove these obnoxious gases allowing maintenance of pleasant inhabitant environments, for example, techniques of removing odor by adsorbing obnoxious gases on activated carbon or impregnated activated carbon containing acids or alkalis have been employed. However, these activated carbons are black and so limitted in their application. For example, when the activated carbons are incorporated in sanitary products such as paper diapers and sanitary napkins which come into direct contact with the skins of human beings, such treatments as not rendering the products black in color to have a clean feel to the products are required, or when the activated carbons are to be incorporated in interior wall sheets, decorations and cosmetics, the products are difficult to impart a desired color so that they are applied to only black products. Moreover, there are problems that the activated carbons has specifically a low ability in deodorization of ammonia and a reduced performance in removing obnoxious gases if they adsorb first moisture.

On the other hand, there have been marketed a variety of adsobents, for example, white ones capable of imparting a clean feel to the products as well as coloring them in desired tinge such as silica gel, zeolite, activated alumina and activated terra abla. However, these white adsorbents have a low deodorizability to the aforementioned obnoxious gases so that they can not be substituted for activated carbons.

As one of the white deodorants, there have been proposed particles having a firmly bonded structure produced with zinc oxide, titanium dioxide and water as disclosed in Japanese Patent Publication (Post-Exam.) No. Hei 3-33022.

According to the disclosure of this Patent, the white deodorants can be produced by preparing a mixed aqueous solution of a water soluble titanium compound and a soluble zinc compound and an alkaline aqueous solution, and combining both the solutions to achieve a pH in the range of 6 to 11 of the mixed solution, thereby effecting neutralization to produce a precipitate comprising zinc oxide, titanium dioxide and water, from which solid particles having a firmly bonded structure of a uniform composition are subsequently formed. In this method, the concentrations of the starting materials such as a titanium compound and the like and the velocity of combining both the solutions must be precisely controlled rendering the operation complicated. In addition, when the pH of the combined solution shifts to outside the defined range, the resultant white deodorant has poor characteristics as disclosed in Japanese Patent Publication (Post-Exam.) No. Hei 3-33022. Moreover, the precipitate produced by the neutralization is in a gel state which tends to be difficult to flitrate, and when dried, the particles of the precipitate may coagulate so firmly that it is difficult to pulverize. Thus, there remain many things to be improved.

SUMMARY OF THE INVENTION

It is an object of the present invention to provide a process for producing conveniently and easily white particles having an excellent deodorizing performance by removing malodorous gases through decomposition and adsorption thereof.

It is another object of the present invention to provide titanium oxide particles comprising particulate titanium oxide substrate having an amount of a zinc oxy compound supported thereon in a molar ratio of the total Ti amount included in the substrate to the Zn amount of said zinc oxy compound, i.e., Ti:Zn=9.9:0.1 to 5:5, said zinc oxy compound being produced by neutralizing a zinc compound with a water soluble compound of alkali metal or alkaline earth metal.

It is still another object of the present invention to provide titanium oxide particles comprising particulate titanium oxide substrate having a zinc oxy compound and a silicon oxy compound supported thereon in a molar ratio of the total Ti amount included in the substrate to the Zn amount of said zinc oxy compound, i.e., Ti:Zn=9.9:0.1 to 5:5, and in a molar ratio of the Zn amount of said zinc compound to the Si amount of said silicon oxy compound, i.e., Zn:Si=9:1 to 0.1:9.9, respectively.

It is still another object of the present invention to provide a process for producing titanium oxide particles comprising particulate titanium oxide substrate having a zinc oxy compound supported thereon, comprising adding a water soluble compound of alkali metal or alkaline earth metal and a zinc compound to a dispersion of the substrate to neutralize the zinc compound in said dispersion, then separating and drying the resultant product.

It is still another object of the present invention to provide a process for producing titanium oxide particles comprising particulate titanium oxide substrate having a zinc oxy compound and a silicon oxy compound supported thereon, comprising adding a zinc compound and a silicon compound and a neutralizing agent to a dispersion of the substrate to neutralize the zinc compound and the silicon compound in said dispersion, then separating and drying the resultant product.

It is still another object of the present invention to provide titanium oxide particles useful as a deodorant or a noxious material scavenger.

DETAILED DESCRIPTION OF PREFERRED EMBODIMENTS

Figure 1:
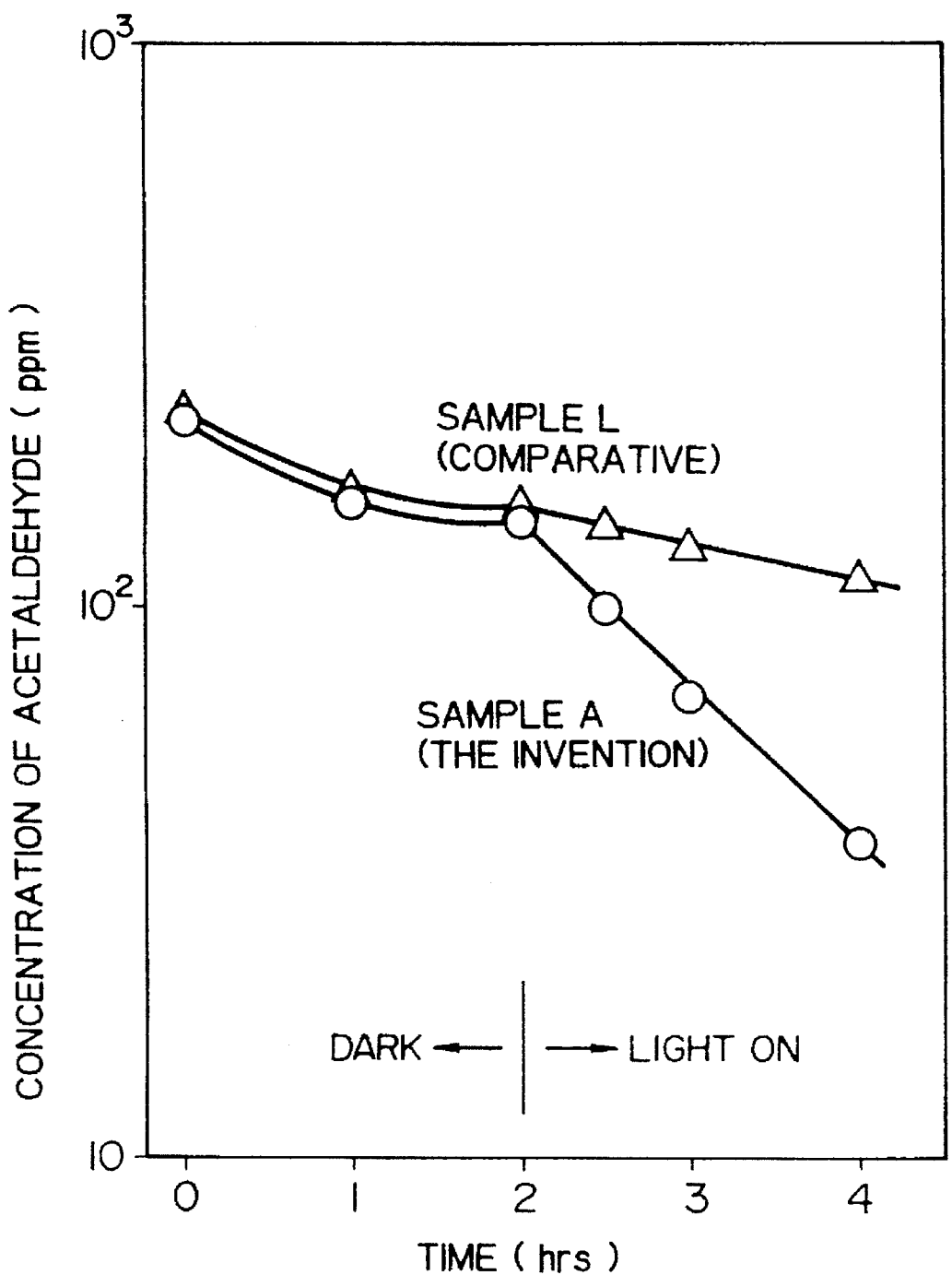
FIG. 1 is a graph showing the experimental results in photocatalytic decomposition of acetaldehyde.

The present inventors have made an intensive research to render titanium oxide more valuable as functional material, during which an interest has been directed to application of titanium oxide to white deodorant. As a result of the proceeded research, it was found that titanium oxide is excellent in performance of removing basic gases such as ammonia and trimethylamine, but poor in removing obnoxious gases such as methyl mercaptan and hydrogen sulfide. After the further strenuous research has been made, it has been found as a result that titanium oxide particles obtained by supporting on particulate titanium oxide substrate the zinc oxy compound which has been produced by neutralizing a zinc compound with a water soluble compound of alkali metals and alkaline earth metals are (1) excellent in the deodorizing performance in removing obnoxious gases, (2) producible through filtration, drying and milling of the product which are easily performed without requiring any complicated operation, and (3) reproducible easily with consistent quality suitable in practical use. The present invention takes into consideration such findings.

In our subsequent research, it was found that when the aforementioned titanium oxide particles supporting zinc oxy compound are used as deodorant in paper diaper, the zinc oxy compound supported on the particulate titanium oxide substrate is dissolved in urine, which results in a reduced deodorizing performance in removing methyl mercaptan, hydrogen sulfide and the like, or which the dissolved zinc ions have a possibility of adversely affecting human beings. Then a further research has been made to overcome the difficulties, and as a result, we have found that if a silicon oxy compound is added to the titanium oxide particles supporting zinc oxy compound, less amount of zinc oxy compound is dissolved and the particles have a high deodorizing performance by removing obnoxious gases, on the basis of which the present invention is derived.

In our additionally subsequent research, it was found that the titanium oxide particles supporting zinc oxy compound, or those supporting in addition silicon oxy compound are capable of removing deleterious materials such as malodorous gases, irritating materials, materials adversely affecting human beings and environment through decomposition thereof by photocatalytic reactions upon irradiation with light including ultraviolet radiation in the presence of oxygen, especially capable of effecting deodorization by removing the malodorous gases through decomposition thereof. The present invention has been accomplished based on the aforementioned findings.

The present invention is concerned with titanium oxide particles comprising particulate titanium oxide substrate having a specific amount of a zinc oxy compound supported thereon, or those having specific amounts of zinc oxy compound and a silicon oxy compound supported thereon. As used herein, the term "titanium oxide" refers also to hydrated titanium oxide besides so-called titanium oxide. The term "zinc oxy compound" refers to zinc oxide and zinc hydroxide. The term "silicon oxy compound" refers to silicon oxide, silicic acid and silicates. As used herein, the term "supported" refers to any condition where the oxy compounds are supported on the substrate, for example, where the zinc oxy compound, silicon oxy compound, or the like are locally or uniformly present on the surfaces of a single substrate particle or a coagulate of substrate particles, or where they are coated in a continuous coating on the surfaces of substrate particles, or where they are taken into the interstices in the substrate particles, so long as the zinc oxy compound, silicon oxy compound and the like are physically or chemically in contact with substrate particles. The amount of the zinc oxy compound to be supported on the particulate titanium oxide substrate may vary depending upon the composition of malodorous gases in consideration. In general, it should be in a molar ratio of the total Ti amount included in the substrate to the Zn amount of the zinc oxy compound, i.e., Ti:Zn=9.9:0.1 to 5:5, more desirably 9.5:0.5 to 7:3. If the amount of the zinc oxy compound to be supported is lower than the defined range, the end product will have undesirably a reduced deodorizing performance in removing methyl mercaptan and hydrogen sulfide. If it is larger than the defined range, the end product will have undesirably a reduced deodorizing performance in removing ammonia and trimethylamine, or an increased amount of free zinc oxide or hydroxide.

The present invention is the titanium oxide particles comprising particulate titanium oxide substrate having the zinc oxy compound and the silicon oxy compound supported thereon where the amount of the silicon oxy compound to be supported may vary depending upon the composition of malodorous gases in consideration. In general, the amount of the zinc oxy compound to be supported should be in a molar ratio of the total Ti amount included in the substrate to the Zn amount of the zinc oxy compound, i.e., Ti:Zn=9.9:0.1 to 5:5, more desirably 9.5:0.5 to 7:3, and the amount of the silicon oxy compound to be supported should be in a molar ratio of the Zn amount of the zinc oxy compound to the Si amount of the silicon oxy compound, i.e., Zn:Si=9:1 to 0.1:9.9, more desirably 9:1 to 4:6. If the amount of the silicon oxy compound to be supported is lower than the defined range, the zinc oxy compound will be liable to dissolve in an aqueous solution, particularly an acidic solution and when used as the deodorant in paper diaper, may undesirably cause a reduction in deodorizing performance or a fear of adversely affecting human beings with the dissolved zinc ions. If the amount of the silicon oxy compound to be supported is larger than the defined range, the end product will have undesirably a reduced deodorizing performance in removing specific malodorous gases though less amount of the zinc oxy compound is dissolved.

When the titanium oxide particles are used especially as deodorant, they should have a specific surface area of 100 $m^2/g$ or more to achieve a good deodorizing speed and higher deodorizing performance. A specific surface area lower than 100 $m^2/g$ results in an substantially insufficient deodorizing performance making it difficult to obtain good deodorants.

According to the process of the present invention, the titanium oxide particles comprising particulate titanium oxide substrate having a zinc oxy compound supported thereon is produced by adding a zinc compound and an alkali to a dispersion of the particulate titanium oxide substrate, to neutralize the zinc compound in said dispersion, then separating and drying the product.

The particulate titanium oxide substrates to be used in the present invention include those obtained by various known methods. As processes for production of particulate titanium oxide substrates, there are, for example, ① a process of hydrolyzing a titanium compound such as titanyl sulfate, titanium chloride and an organic titanium compound under heat, if necessary, in the presence of seed for nucleation, ② a process of neutralizing a titanium compound such as titanyl sulfate, titanium chloride and an organic titanium compound by adding an alkali thereto, ③ a process of oxidizing titanium chloride, an organic titanium compound and the like in a vapor phase, and ④ a process of calcining the titanium oxide obtained in the aforementioned processes ①, or ② at a temperature of about 600° C. or less.

In the process of the present invention, the particulate titanium oxide substrate is dispersed in a solvent such as water, and if necessary, classified, to produce a dispersion.

To the dispersion, there is added a zinc compound which may be any one of various zinc compounds such as zinc chloride, zinc sulfate, zinc nitrate and the like. The alkalis to be used include desirably water soluble compounds of alkali metals and alkaline earth metals such as sodium hydroxide, potassium hydroxide, sodium carbonate, sodium bicarbonate, sodium silicate, and barium hydroxide. The use of ammonia or ammonium salts as alkalis is undesirable, because they have a tendency to form complex ions with the zinc compounds causing dissolution of zinc oxide. The neutralization of the zinc compounds in the dispersion of the particulate titanium oxide substrate may be performed by any one of procedures of, for example, adding simultaneously the zinc compound and the alkali to said dispersion, or adding the zinc compound to said dispersion and then adding the alkali, or adding the alkali to said dispersion and then adding the zinc compound. The zinc oxy compound is generally precipitated by conducting neutralization at a pH in the range of 6 to 11. The conditions of the concentration of the particulate titanium oxide substrate in the dispersion, the amount of the zinc compounds or the alkalis to be added, the concentration of each of them when used as an aqueous solution, the speed of addition, and the temperature at the neutralization reaction are not critical, but can optionally be set. Prior to the neutralization reaction, any one of dispersants such as orthophosphoric acid, pyrophosphoric acid, hexametaphosphoric acid, alkali salts thereof, sodium orthosilicate, and sodium metasilicate may be added to the dispersion, provided that the deodorizing performance of the titanium oxide particles is not adversely affected, in order to improve the distribution of the particulate titanium oxide substrate in the dispersion thereof.

The product produced in this way is separated and, if necessary, washed, and then dried. The separation may be effected by normal filtration or decantaion. The drying may be effected at a temperature of 100° to 600° C., preferably 100° to 200° C. The dried product may be disintegrated or ground to produce powders, or shaped into granules for the end uses.

An increased amount of the zinc oxy compound supported on the particulate titanium oxide substrate tends to reduce the specific surface area of the titanium oxide particles. It is desired, therefore, to employ such particulate titanium oxide substrate as having a specific surface area of larger than 100 $m^2/g$ in order to produce titanium oxide particles having a specific surface area of larger than 100 $m^2/g$.

In the process of the present invention, the titanium oxide particles comprising particulate titanium oxide substrate having zinc oxy compound and a silicon oxy compound supported thereon can be produced in accordance with the process as described above for making zinc oxy compound supported on the particulate titanium oxide substrate. That is, a zinc compound, a silicon compound and a neutralizing agent are added to the dispersion of particulate titanium oxide substrate to neutralize the zinc compound and the silicon compound in the dispersion to produce a product which is separated and dried. The silicon compounds to be used include various silicon compounds such as water-glass, sodium orthosilicate, sodium metasilicate, and silicon chloride. The neutralizing agents include various acids such as hydrochloric acid, sulfuric acid, and nitric acid. The neutralization of the silicon compounds may be effected according to the neutralization process as described above for the neutralization of the zinc compounds, generally at a pH in the range of about 6 to 11 to produce a precipitate. The zinc compounds and the silicon compounds may be simultaneously neutralized, or alternatively, separately neutralized.

The simultaneous neutralization results in coprecipitation of a zinc oxy compound and a silicon oxy compound which are supported on the particulate titanium oxide substrate. In effecting separately each neutralization, for example, the zinc oxy compound is supported on the particulate titanium oxide substrate, followed by making the silicon oxy compound supported thereon. When the titanium oxide particles according to the present invention are used as deodorant, one of the most preferred process for the production thereof is to neutralize or hydrolyze a titanium compound with an alkali to produce particulate titanium oxide substrate in the liquid phase, followed by adding simultaneously a zinc compound, a silicon compound and a neutralizing agent to the liquid dispersion of the particulate titanium oxide substrate to produce the titanium oxide particles having a zinc oxy compound and a silicon oxy compound supported thereon.

The conditions of the concentration of the particulate titanium oxide substrate in the dispersion, the amounts of the silicon compounds, the zinc compounds and the alkalis to be added, the concentration of each of them when used as an aqueous solution, the speed of addition, and the temperature at the neutralization reaction are not critical, but can optionally be selected.

The product produced in this way is separated and, if necessary, washed, and then dried in accordance with the identical procedure to that described above for supporting the zinc oxy compound. The separation may be effected by normal filtration or decantation. The drying may be effected at a temperature of 100° to 600° C., preferably 100° to 200° C. The dried product may be disintegrated or ground to produce powders, or shaped into granules for the end uses.

According to the present invention the titanium oxide particles comprising the particulate titanium oxide substrate having a zinc oxy compound supported thereon or the titanium oxide particles comprising the particulate titanium oxide substrate having a zinc oxy compound and a silicon oxy compound may be used alone as deodorant or as noxious material scavenger, or alternatively, may be used in combination with ordinary materials which have been used in the art such as aluminum oxide, zeolite and the like.

Various malodorous gases can effectively be removed by contacting them with the deodorants of the present invention. In addition, various deleterious materials can effectively be converted into non-deleterious materials by contacting them with the scavengers of the present invention under irradiation of light including ultraviolet radiation in the presence of oxygen. The ultraviolet radiations to be used in the present invention are preferably near ultraviolet radiations having a wavelength in the range of 300 to 400 nm. The deleterious material scavengers of the present invention can apply to a wide variety of obnoxious materials such as malodorous materials, irritating materials, and other materials which adversely affect human beings and their life environment. Examplary functions of the scavengers are decomposition of the aforementioned malodorous gases and air-polluting gases such as nitrogen oxides, sulfur oxides, and water-polluting materials such as oils, and other organic compounds such as polybiphenyl chloride and dioxine as well as sterilization.

When the titanium oxide particles of the present invention are used as a noxious material scavenger or deodorant capable of decomposing noxious materials by a photocatalytic reaction, the particles should preferably have a specific surface area of 100 $m^2/g$ or more, more preferably 150 $m^2/g$ or more, most preferably 200 $m^2/g$ or more. If the specific surface area is less than 100 $m^2/g$, then the photocatalytic reaction is effected with a reduced efficiency, so that they cannot appropriately be used as the noxious material scavenger or deodorant.

Moreover, the titanium oxide particles comprising particulate titanium oxide substrate having a zinc oxy compound are useful for pigments, catalysts, catalyst supports, adsorbents and the like. Particularly, they are excellent in deodorizing performance by removing malodorous gases such as ammonia, methyl mercaptan, hydrogen sulfide, trimethylamine, methyl sulfide, acetaldehyde and the like through decomposition thereof and useful for white deodorants capable of deodorizing sanitary objects such as paper diaper and sanitary napkins which are directly in contact with skins of human beings.

Furthermore, the titanium oxide particles can effectively and promptly remove deleterious materials by photocatalytic reactions so that they are quite useful as deodorants not only for industrial use but also for ordinary domestic use. The noxious material scavengers of the present invention find application to a wide variety of deleterious materials and are highly safe to be disposable without polluting the environment so that they are very useful in industry.

The process of the present invention can conveniently and easily produce stable quality titanium oxide particles and is extremely useful in industry in that the product is relatively rapidly filtrable and washable during the production thereof and the particulate mass produced after drying can be easily disintegrated and readily pulverized.

The present invention will be described with reference to some Examples and Comparative Examples together with accompanying drawings.

EXAMPLE 1

Ten liters of a 2 mol/l solution of titanyl sulfate were hydrolyzed under heat in the presence of seeds for nucleation to produce a precipitate. The precipitate was subsequently flitrated, washed, and dried to produce particulate titanium oxide substrate which had a specific surface area of 290 m$^2$/g as determined by the B.E.T. method (as used hereinunder).

Then 80 grams of the particulate titanium oxide substrate were dispersed in one liter of pure water, and heated to a temperature of 40° C., followed by the dropwise addition of a 2N aqueous solution of sodium hydroxide to control the pH of the dispersion at 8. Then with stirring, to the dispersion there were added dropwise simultaneously 110 ml of a 1 mol/l aqueous solution of zinc chloride and a 2N aqueous solution of sodium hydroxide over 10 minutes while maintaining the pH of the dispersion at 8 to yield a product. Subsequently the product was filtered, washed, dried at a temperature of 120° C., and then disintegrated to yield titanium oxide. particles according to the present invention (Sample A).

EXAMPLE 2

The same procedure as in Example 1 was repeated, except that 50 ml of the aqueous solution of zinc chloride were added dropwise, to yield titanium oxide particles of the present invention (Sample B).

EXAMPLE 3

The same procedure as in Example 1 was repeated, except that 430 ml of the aqueous solution of zinc chloride were added dropwise, to yield titanium oxide particles of the present invention (Sample C).

EXAMPLE 4

80 grams of the particulate titanium oxide substrate produced according to the process as described in Example 1 were dispersed in one liter of pure water. To the dispersion was added 15 grams of powdery zinc chloride, followed by heating to a temperature of 40° C. Then, to the dispersion with stirring there were added dropwise a 2N aqueous solution of sodium hydroxide over 10 minutes to control the pH of the dispersion at 8 to produce a product. Subsequently the product was filtered, washed, dried at a temperature of 120° C., and then disintegrated to yield titanium oxide particles according to the present invention (Sample D).

EXAMPLE 5

80 grams of the particulate titanium oxide substrate produced according to the process as described in Example 1 were dispersed in one liter of pure water. To the dispersion was added 8.9 grams of sodium hydroxide, followed by heating to a temperature of 40° C. Then, to the dispersion with stirring there were added dropwise 110 ml of a 1 mol/l aqueous solution of zinc chloride over 10 minutes to control eventually the pH of the dispersion at 8 to produce a product. Subsequently the product was filtered, washed, dried at a temperature of 120° C., and then disintegrated to yield titanium oxide particles according to the present invention (Sample E).

EXAMPLE 6

One liter of a 1 mol/l aqueous solution titanium tetrachloride was hydrolyzed under heat in the presence of seeds for nucleation to produce a titanium oxide precipitate. (The titanium oxide precipitate after filtered, washed and dried had a specific surface area 160 m$^2$/g.)

After the thus produced dispersion of particulate titanium oxide substrate was conditioned to a temperature of 40° C., to the dispersion was added dropwise a 2N aqueous solution of sodium hydroxide to control the pH of the dispersion at 8. Then with stirring, to the dispersion there were added dropwise simultaneously 110 ml of a 1 mol/l aqueous solution of zinc chloride and a 2N aqueous solution of sodium hydroxide over 10 minutes while maintaining the pH of the dispersion at 8 to yield a product. The product was filtered, washed, dried at a temperature of 120° C., and then disintegrated to yield titanium oxide particles according to the present invention (Sample F).

COMPARATIVE EXAMPLE 1

One liter of a 1 mol/l aqueous solution of zinc chloride was heated to a temperature of 40° C., to which solution with stirring, was added dropwise a 2N aqueous solution of sodium hydroxide over 100 minutes to control the pH of the aqueous solution at 8 to yield a product. The product was filtered, washed, dried at a temperature of 120° C., and then disintegrated to yield zinc hydroxide particles (Sample G).

COMPARATIVE EXAMPLE 2

The titanium oxide produced by the process in Example 1 without effecting any other treatment was used as Sample H.

In all the Examples 1 to 6, the filtration and washing of the precipitates could be relatively rapidly achieved and the powdery products after drying were easily disintegrated and easily pulverized.

The specific surface areas and the adsorption rates of the Samples A to H obtained in Examples and Comparative Examples are reported in Table 1.

The following procedure was used to evaluate the Samples for the adsorption of malodorous gases: First each of trimethylamine, methyl mercaptan and hydrogen sulfide were diluted with nitrogen gas to about 1000 ppm. Then one liter of the diluted gas was introduced into a polyester bag containing 0.1 gram of the Sample and after sealed, left to stand for 5 hours. Thereafter, the concentration of the malodorous gases remaining in the bag was measured by a gas chromatography or a gas sensor and the adsorption rates were calculated from the concentration values of the diluted gases introduced.

EXAMPLE 9

The identical procedure to that in Example 7 was repeated, except that no sodium orthosilicate was added, to yield titanium oxide particles of the present invention (Sample K).

The specific surface areas and the adsorption rates of the Samples I to K obtained in Examples were measured and the results are set forth in Table 2. It can be found that the Samples are excellent in adsorption rate with malodorous gases and preferred as white deodorants.

Next, one gram of each of the Samples was dispersed in 100 ml of a 0.01N aqueous solution of hydrochloric acid and

TABLE 1

|  | Sample | Molar ratio Ti:Zn | Color of particles | Surface area ($m^2/g$) | Percent gas adsorption (%) | | |
| --- | --- | --- | --- | --- | --- | --- | --- |
|  |  |  |  |  | Trimethylamine | Methyl mercaptan | Hydrogen sulfide |
| Example 1 | A | 9:1 | White | 235 | 63.4 | 99.7 | 100 |
| Example 2 | B | 9.5:0.5 | White | 242 | 73.4 | 91.8 | 100 |
| Example 3 | C | 7:3 | White | 174 | 57.2 | 99.3 | 100 |
| Example 4 | D | 9:1 | White | 237 | 61.6 | 99.5 | 100 |
| Example 5 | E | 9:1 | White | 228 | 60.4 | 98.8 | 100 |
| Example 6 | F | 9:1 | White | 144 | 42.9 | 65.8 | 100 |
| Comparative Example 1 | G | 0:10 | White | 26 | 16.6 | 35.7 | 100 |
| Comparative Example 2 | H | 10:0 | White | 290 | 60.0 | 10.7 | 10.0 |

EXAMPLE 7

150 ml of a 1 mol/l aqueous solution of titanium tetrachloride were heated to a temperature of 40° C., to which solution with stirring a 4N aqueous solution of sodium hydroxide was added dropwise over 10 minutes to control the pH of the aqueous solution at 3 to produce a titanium oxide precipitate.

To the dispersion of particulate titanium oxide substrate with stirring, there were added dropwise simultaneously 50 ml of a 3 mol/l aqueous solution of zinc chloride, 36.8 grams of sodium orthosilicate and a 4N aqueous solution of sodium hydroxide over 10 minutes while maintaining the pH of the dispersion at 8 to yield a product. The product was filtered, washed, dried at a temperature of 120° C., and then disintegrated to yield titanium oxide particles according to the present invention (Sample I).

EXAMPLE 8

The identical procedure to that in Example 7 was repeated, except that 225 ml of the aqueous solution of titanium tetrachloride, 75 ml of the aqueous solution of zinc chloride and 9.2 grams of sodium orthosilicate, to yield titanium oxide particles of the present invention (Sample J).

100 ml of a 0.01N aqueous solution of sodium hydroxide, respectively, agitated for 3 hours at a temperature of 40° C., and then the supernatant was removed to evaluate the amount of zinc ions present therein by an emission spectroscopy. The results are shown in Table 3. It can be seen that Samples I and J are soluble in an alkaline aqueous solution to almost the same extent, but less soluble in an acidic aqueous solution as compared with Sample K.

TABLE 2

|  | Sample | Molar ratio Ti:Zn:Si | Color of particles | Surface area ($m^2/g$) | Percent gas adsorption (%) | | |
| --- | --- | --- | --- | --- | --- | --- | --- |
|  |  |  |  |  | Trimethylamine | Methyl mercaptan | Hydrogen sulfide |
| Example 7 | I | 3:3:4 | White | 297 | 56.1 | 89.6 | 100 |
| Example 8 | J | 4.5:4.5:1 | White | 299 | 64.4 | 99.3 | 100 |
| Example 9 | K | 5:5:0 | White | 206 | 62.6 | 99.1 | 100 |

TABLE 3

|  | Sample | Concentration of zinc ions (expressed by ZnO) (mg/l) | |
| --- | --- | --- | --- |
|  |  | Aqueous hydrochloric acid solution | Aqueous sodium hydroxide solution |
| Example 7 | I | 200 | 1 or less |
| Example 8 | J | 280 | 1 or less |
| Example 9 | K | 400 | 1 or less |

COMPARATIVE EXAMPLE 3

A mixed solution of 100 ml of a 1 mol/l aqueous solution of zinc chloride and 900 ml of a 1 mol/l aqueous solution of titanium tetrachloride was heated to a temperature of 40° C., to which solution with stirring a 4N aqueous solution of sodium hydroxide was added dropwise at a rate of 10 ml/min. to control the pH of the mixed solution at 8 to yield a product. The product was filtered, washed, dried at a temperature of 120° C., and then disintegrated to yield particles of titanium oxide and zinc hydroxide (Sample L).

The Samples A and L obtained in Example and Comparative Example were evaluated for ability of photocatalytically decomposing malodorous gases.

First, 0.1 gram of each of the Samples was dispersed in 5 ml of ethanol and the dispersion was poured into a schale of a diameter of 8.6 cm and dried at a temperature of 70° C. to be deposited uniformly on the bottom surface of the schale. These schales were placed in a closed plastic vessel having a inner volume of about 8 liters equipped with 4 W black light, into which acetaldehyde and methyl mercaptan were injected, respectively. Then after leaving to stand for 2 hours under dark, the black light was turned on to effect a photocatalytic reaction and the variation in the concentration of malodorous gases in the inside of the closed vessel was determined by a gas chromatography. The irradiation intensity of the light having a wavelength in the range of 310 to 400 nm was about 1 mW/cm$^2$.

Figure 2:
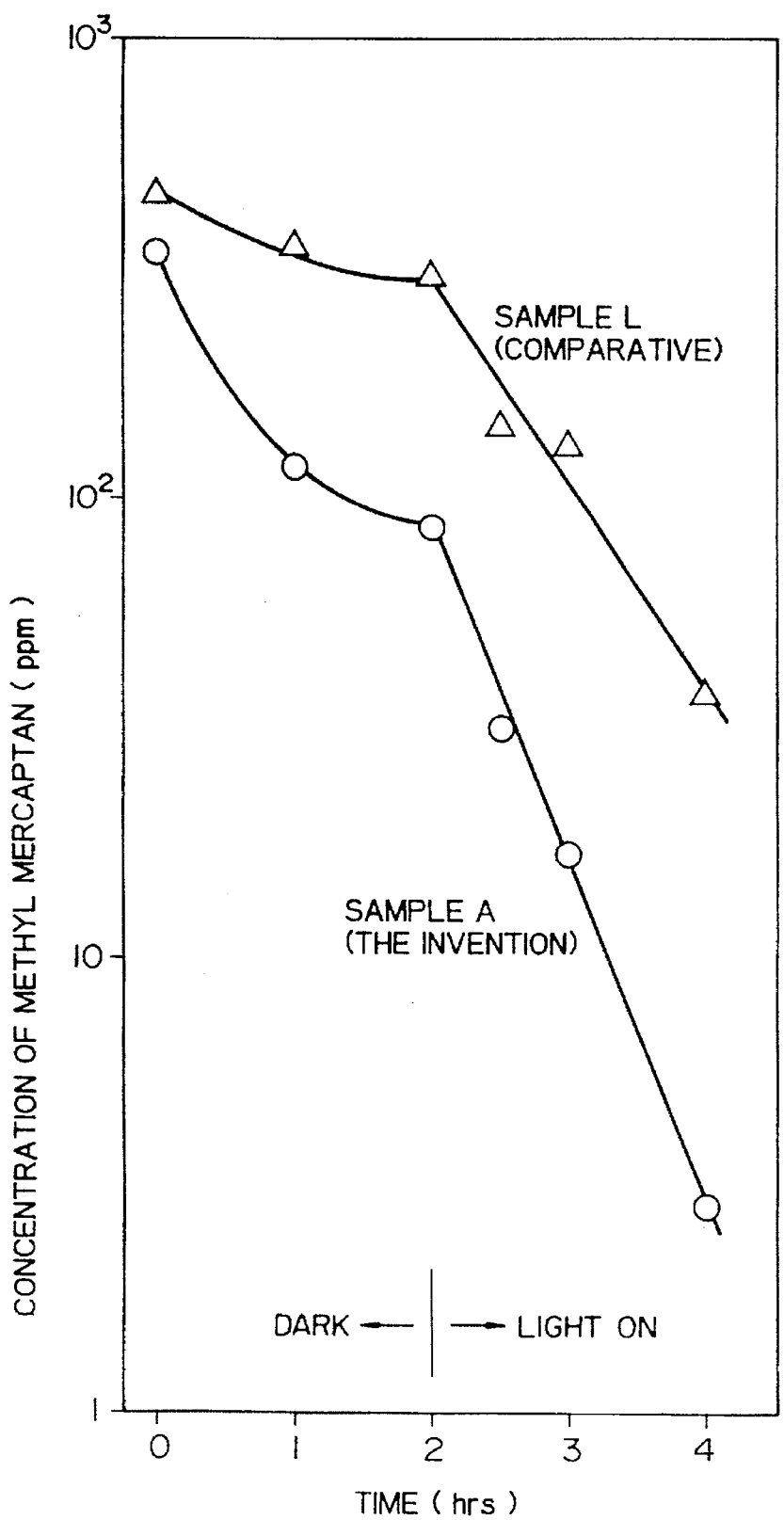
FIG. 2 is a graph showing the experimental results in photocatalytic decomposition of methyl mercaptan.

The photocatalytic decomposition of acetaldehyde is shown in FIG. 1 and that of methyl mercaptan in FIG. 2. The kinetics of the photocatalytic reaction with the black light being turned on were determined from the slope of the linear portion of the curves shown in FIGS. 1 and 2, the results of which are indicated in Table 4.

TABLE 4

| | | Rate constant (min$^{-1}$) | |
|---|---|---|---|
| | Sample | Acetaldehyde | Methyl mercaptan |
| Example 1 | A | $4.7 \times 10^{-3}$ | $1.2 \times 10^{-2}$ |
| Comparative Example 3 | L | $1.0 \times 10^{-3}$ | $7.2 \times 10^{-3}$ |

What is claimed is:

1. A method of scavenging a noxious material which comprises, applying to noxious materials in need of scavenging, a scavengingly effective amount of a noxious material scavenger, and decomposing the noxious materials by a photocatalytic reaction, said scavenger comprising:

particulate titanium oxide substrate having a zinc oxy compound supported thereon in a molar ratio of the total Ti amount included in the substrate to the Zn amount of the zinc oxy compound, i.e., Ti:Zn=9.9:0.1 to 5:5, said zinc oxy compound being produced by neutralizing a zinc compound with a water soluble compound of alkali metal or alkaline earth metal, said particulate titanium oxide substrate having a specific surface area of 100 m$^2$/g or more, wherein said scavenger decomposes noxious materials by a photocatalytic reaction.

2. A method of decomposing malodorous gases which comprises, applying to the malodorous gases an amount of a deodorant effective to decompose the malodorous gases, and decomposing the malodorous gases by a photocatalytic reaction, said deodorant comprising:

particulate titanium oxide substrate having a zinc oxy compound supported thereon in a molar ratio of the total Ti amount included in the substrate to the Zn amount of the zinc oxy compound, i.e., Ti:Zn= 9.9:0.1 to 5:5, said zinc oxy compound being produced by neutralizinq a zinc compound with a water soluble compound of alkali metal or alkaline earth metal, said particulate titanium oxide substrate having a specific surface area of 100 m$^2$/g or more, wherein said deodorant decomposes malodorous gases by a photocatalytic reaction.

* * * * *